United States Patent [19]

Keenan et al.

[11] Patent Number: 5,596,007
[45] Date of Patent: Jan. 21, 1997

[54] THERAPEUTIC METHOD TO ALLEVIATE THE CRAVING ASSOCIATED WITH CESSATION OF TOBACCO WITH COTININE

[75] Inventors: Robert M. Keenan, Baltimore, Md.; Dorothy K. Hatsukami, Golden Valley, Minn.

[73] Assignee: Pharmaco Behavioral Associates, Inc., Minneapolis, Minn.

[21] Appl. No.: 885,314

[22] Filed: May 18, 1992

[51] Int. Cl.$^6$ .................................................. A61K 31/44
[52] U.S. Cl. .................................................. 514/343
[58] Field of Search .................................. 514/339, 343; 546/281, 282

[56] References Cited

U.S. PATENT DOCUMENTS

| | | | |
|---|---|---|---|
| 2,981,641 | 4/1961 | O'Neill | 131/17 |
| 3,048,520 | 8/1962 | Mckennis, Jr. et al. | 167/65 |
| 3,821,960 | 7/1974 | Egri | 131/143 |
| 3,867,519 | 2/1975 | Michaels | 424/473 |
| 3,870,791 | 3/1975 | Haddad et al. | 424/427 |
| 3,870,794 | 3/1975 | Hutchinson et al. | 424/264 |
| 4,051,842 | 10/1977 | Hazel et al. | 128/640 |
| 4,136,177 | 1/1979 | Lin et al. | 514/114 |
| 4,140,122 | 2/1979 | Kuhl et al. | 604/890.1 |
| 4,255,415 | 3/1981 | Chrai et al. | 514/40 |
| 4,383,529 | 5/1983 | Webster | 604/20 |
| 4,621,074 | 11/1986 | Bourne | 514/12 |
| 4,668,506 | 5/1987 | Bawa et al. | 424/429 |
| 4,713,244 | 12/1987 | Bawa et al. | 424/429 |
| 4,748,181 | 5/1988 | Hutchinson et al. | 514/343 |
| 4,788,063 | 11/1988 | Fisher et al. | 424/449 |
| 4,835,162 | 5/1989 | Abood | 514/305 |
| 4,931,279 | 6/1990 | Bawa et al. | 424/427 |
| 4,946,853 | 8/1990 | Bannon et al. | 514/343 |
| 4,966,916 | 10/1990 | Abood | 514/534 |
| 5,187,169 | 2/1993 | Lippiello et al. | 514/343 |
| 5,298,257 | 3/1994 | Bannon et al. | 424/449 |

FOREIGN PATENT DOCUMENTS

| | | |
|---|---|---|
| 273715 | 2/1964 | France . |
| 2428M | 3/1964 | France . |

OTHER PUBLICATIONS

"Tobacco Organic Mental Disorder, Caffeine Organic Mental Disorder, Tobacco Dependence", *Diagnostic and Statistical Manual of Mental Disorders, 3rd Edition*, American Psychiatric Assoc., Washington, D.C., pp. 159–160, 176–178, (1980).

K. E. Bauman, et al., "On the Measurement of Tobacco Use by Adolescents", *Am. J. Epidemiol.*, 130, 327–337, (1989).

M. E. Carroll, et al., "Nicotine Dependence in Rats", *Life Sciences*, 45, 1381–1388, (1989).

M. Curvall, et al., "The pharmacokinetics of cotinine in plasma and saliva from non–smoking healthy volunteers", *Eur. J. Clin. Pharmacol.*, 38, 281–287, (1990).

E. DiGuisto, et al., "Some Properties of Saliva Cotinine Measurements in Indicating Exposure to Tobacco Smoking", *AJPH*, 1986, 1245–1246, (1986).

D. F. Glenn, et al., "Synthesis and Mass Spectroscopy of Some Structurally Related Nicotinoids", *J. Org. Chem.*, 43, 2860–2870, (1978).

N. W. Heimstra, et al., "The Effects of Deprivation of Cigarette Smoking on Psychomotor Performance", *Ergonomics*, 23, 1047–1055, (1980).

R. R. Hutchinson, et al., "Effects of nicotine on avoidance, conditioned suppression and aggression response measures in animals and man", In: *Smoking Behavior: Motives and Incentives*, W. L. Dunn (ed.), V. H. Winston & Sons, Washington, D.C., pp. 171–196, (1973).

J. R. Idle, "Titrating Exposure to Tobacco Smoke Using Cotinine—A Minefield of Misunderstandings", *J. Clin. Epidemiol.*, 43, 313–317, (1990).

L. Jarczyk, et al., "Serum and Saliva Concentrations of Cotinine on Smokers and Passive Smokers", *J. Clin. Chem. Clin. Biochem.*, 27, 230–231, (1989).

M. Jarvis, et al., "Biochemical Markers of Smoke Absorption and Self Reported Exposure to Passive Smoking", *J. Epidemiol. Commun. Health*, 38, 335–339, (1984).

J. S. Jordanov, "Cotinine Concentrations in Amniotic Fluid and Urine of Smoking, Passive Smoling and Non–Smoking Pregnant Women at Term and in the Urine of the Neonates on 1st Day of Life", *Eur. J. Pediatr.*, 149, 734–737, (1990).

W. R. Martin, et al., "Physiologic, Subjective, and Behavioral Effects of Amphetamine, Methamphetamine, Ephedrine, Phenmetrazine, and Methylphenidate in Man", *Clinical Pharmacol. and Therapeut.*, 12, 245–258, (1971).

H. McKennis, et al., "Demethylation of Cotinine in vivo", *J. Am. Chem. Soc.*, 81, 3951–3954, (1959).

A. D. McNeill, et al., "Saliva Cotinine as an Indicator of Cigarette Smoking in Adolescents", *Brit. J. Addiction*, 82, 1355–1360, (1987).

M. P. Noland, et al., "Saliva Cotinine and Thiocyanate: Chemical Indicators of Smokeless Tobacco and Cigarette Use in Adolecents", *J. Behavioral Med.*, 11, 423–433, (1988).

(List continued on next page.)

*Primary Examiner*—Kevin E. Weddington
*Attorney, Agent, or Firm*—Schwegman, Lundberg, Woessner & Kluth, P.A.

[57] ABSTRACT

A therapeutic method is provided to alleviate tobacco withdrawal syndrome and/or the symptoms of nicotine withdrawal, comprising administering an amount of cotinine or a pharmaceutically acceptable salt thereof to a human in need of such treatment, which amount is effective to reduce or eliminate at least one of the symptoms of tobacco withdrawal syndrome or nicotine withdrawal.

26 Claims, No Drawings

OTHER PUBLICATIONS

B. Testa, et al., "Circular Dichroic Determination of the Preferred Conformation of Nicotine and Related Chiral Alkaloids in Aqueous Solution", *Molecular Pharmacology*, 9, 10–16, (1973).

S. G. Thompson, et al., "Relation of Urinary Cotinine Concentrations to Cigarette Smoking and to Exposure to Other People's Smoke", *Thorax*, 45, 356–361, (1990).

S. T. Tiffany, et al., "The Development and Initial Validation of a Quesionaire on Smoking Urges", *Brit. J. Addiction*, 86, 1467–1476, (1991).

H. Van Vunakis, et al., "Decreased Serum Cotinine Levels in Smokers of Both Tobacco and Marijuana as Compared with Smokers of Tobacco Only", *Pharmacol. Biochem. Behav.*, 30, 895–898, (1988).

L. E. Wagenknecht, et al., "Racial Differences in Serum Cotinine Levels Among Smokers in the Coronary Artery Risk Development in (Young) Adults Study", *AJPH*, 80, 1053–1056, (1990).

P. Zeidenberg, et al., "Abstracts of Niocine: cotinine levels in blood during cessation of smoking", *Comp. Psychiatry*, 18, 93–111, (1977).

M. E. Carroll et al., *Life Sci.*, 45, 1381 (1989).

L. Abood et al., "Specific Binding and Metabolism of (−)- and (+)-[3H]-Nicotine in Isolated Rat Hepatocytes and Hepatocyte Membranes", *Arch. Int. Pharmacodyn*, 723:62–73 (1985).

R. Barbieri et al., "Nicotine, Cotinine and Anabasine Inhibit Aromatase in Human Trophoblast in Vitro", *J. Clin. Invest.*, 77:1727–1733 (1986).

R. Barbieri et al., "The Effects of Nicotine, Cotinine, and Anabasine on Rat Adrenal 11–beta–hydroxylase and 21–hydroxylase", *J. Steroid Biochem.*, 28:25–28 (1987).

N. Benowitz, "The Use of Biologic Fluid Samples in Assessing Tobacco Smoke Consumption", *Measurement in the Analysis and Treatment of Smoking Behavior*, J. Grabowski et al. eds., NIDA Research Monograph No. 48, U.S. DHHS, PHS, ADAMHA (1983).

N. Benowitz et al., "Continine Disposition and Effects", *Clin. Pharmacol. Ther.*, 34:604–611 (1983).

N. Benowitz et al., "Inverse Relation Between Serum Cotinine Concentration and Blood Pressure in Cigarette Smokers", *Circulation*, 80:1309–1312 (1989).

J. Borzelleca et al., "Studies on the Respiratory and Cardiovascular Effects of (−)–Cotinine", *J. Pharm. Exper. Therapeutics*, 137:313–318 (1962).

E. Bowman et al., "(−)–Cotinine", *Biochem. Preparations*, 10:36–39 (1963).

E. Bowman et al., "Studies on the Metabolism of (−)–Cotinine in the Human", *J. Pharmacol. Exp. Ther.*, 135:306–311 (1962).

E. Bowman et al., "Disposition and Fate of (−)–Citubube–H3 in the Mouse", *J. Pharmac. Exper. Therapeutics*, 143:301–308 (1964).

R. Chahine et al., "The in Vitro Effects of Nicotine an Cotinine on Prostacyclin and Thromboxane Biosynthesis", *Prostaglandins, Leukotrienes, and Essential Fatty Acids*, 40:261–266 (1990).

M. Curvall et al., "Monitoring Absorption by Means of Determination of Nicotine and Cotinine", *Arch. Toxicol. Suppl.*, 9:88–102 (1986), Abstract.

D. Dawson et al., "Evaluation of the Developmental Toxicity of Nicotine and Cotinine with Frog Embryo Teratogenesis Assay: Xenopus", *Teratogenesis, Carcinogenesis and Mutagenesis*, 8:329–338 (1988).

P. DeSchepper et al., "Kinetics of Cotinine After Oral and Intravenous Administration to Man", *Eur. J. Pharmacol.*, 31:583–588 (1987).

P. Dominiak et al., "Effects of Nicotine and its Major Metabolites on Blood Pressure in Anesthetized Rats", *Klinische Wochenschrift*, 63:90–92 (1985).

N. Edwards et al., "Doxepin as an Adjunct to Smoking Cessation: A Double–Blind Pilot Study", *Am. J. Psychiatry*, 146/3:373–376 (Mar. 1989).

W. Frankenburg et al., "The Chemistry of Tobacco Fermentation. I. Conversion of the Alkaloids D. Identification of Cotinine in Fermented Leaves", *Cotinine in Fermented Tobacco Leaves*, 79:149–151 (Jan. 1957).

K. Fuxe et al., "On the Action of Nicotine and Cotinine on Central 5–Hydroxytryptamine Neurons", *Pharmacology, Biochem. & Behavior*, 10:671–677 (1979).

S. Goldberg et al., "Nicotine and Some Related Compounds: Effects on Schedule–Controlled Behavior and Discriminative Properties in Rats", *Psychopharmacology*, 97:295–302 (1989).

D. Hatsukami et al., "Effects of Nicotine Gum on Prevalence and Severity of Withdrawal in Female Cigarette Smokers", *J. Substance Abuse*, 3:427–440 (1991).

J. Hughes et al., "Signs and Symptoms of Tobacco Withdrawal", *Archives of General Psychology*, 43:289–294 (1986).

J. Hughes et al., "Effects of Abstinence from Tobacco", *Research and Advances in Alcohol and Drug Problems*, vol. 10 at pp. 317–398, L. T. Kozlowski et al., eds., Plenum Pub. Corp. (1990).

K. Kim et al., "Effects of Some Nicotine Metabolites and Related Compounds on Isolated Smooth Muscle", *J. Pharm. Exper. Therapeutics*, 161:59–69 (1968).

G. Kyerematen et al., "Time–Dependent Induction of Hepatic Drug Metabolism in Rats by Cotinine", *Life Sciences*, 32:551–556 (1983).

E. LaVoie et al., "Evaluation of the Effects of Cotinine and Nicotine–N'–Oxides on the Development of Tumors in Rats Initiated with N–[4–(5–Nitro–2–furyl)–2–thiazolyl] formamide", *J. Natl. Cancer Inst.*, 75:1075–1081 (1985).

H. McKennis Jr. et al., "N–Methylation of Nicotine and Cotinine in Vivo", *J. Biol. Chem.*, 238:719–723 (1963).

H. McKennis Jr. et al., "Alternate Routes in the Metabolic Degradation of the Pyrrolidine Ring of Nicotine", *J. Biol. Chem.*, 239:3990–3996 (1964).

A. Meikle et al., "Nicotine and Cotinine Effects on 3–alpha Hydroxysteroid Dehydrogenase in Canine Prostate", *Life Sciences*, 43:1845–1850 (1988).

Office of Smoking and Health, *The Health Consequences of Smoking: Nicotine Addiction. A Report to the Surgeon General*, U.S. Govt. Print. Off., Washington D.C., DHHS Pub. No. (CDC) 88–8406, pp. 197–208 (1988).

T. Patterson et al., "Nicotine and Cotinine Inhibit Steroidogenesis in Mouse Leydig Cells", *Life Sciences*, 46:265–272 (1990).

Rahn et al., "Correlations Between Urinary Nicotine and Cotinine and Urinary Mutagenicity in Smokers on Controlled Diets", *Environ. Molec. Mutagenesis*, 17:244–252 (1991).

Riebe et al., "Mutagenicity Testing in Bacterial Tests Systems of Some Constituents of Tobacco", *Mutation Research*, 101:39–43 (1981).

M. Risner et al., "Effects of Nicotine, Cocaine and Some of Their Metabolites on Schedule–Controlled Responding by Beagle Dogs and Squirrel Monkeys", *J. Pharmacol. and Exp. Ther.*, 234:113–119 (1985).

Scherer et al., "Pharmacokinetics of Nicotine, Cotinine, and 3'-hydroxycotinine in Cigarette Smokers", *Klinische Wochenschrift*, 66(SuppX1):5–11 (1988).

S. Schwartz et al., "Studies on the Degradation of the Pyrrolidine Ring of (–)-Nicotine in Vivo", *J. Biol. Chem.*, 238:1807–1812 (1963).

D. Sepkovic et al., "Biomedical Applications of Cotinine Quantitation in Smoking Related Research", *AJPH*, 75:663–665 (1985).

Srivastava et al., "Effect of Nicotine and Cotinine on the Production of Oxygen Free Radicals by Neutrophils in Smokers and Non–Smokers", *Human Toxicology*, 8:461–463 (1989).

Weiss et al., "Cotinine Levels in Follicular Fluid and Serum of IVF Patients: Effect on Granulosa–luteal Cell Function in Vitro", *Human Reproduction*, 4:482–485 (1989).

K. Yamamoto et al., "Nicotine–Induced EEG and Behavioral Arousal", *Intern. J. Neuropharmacol.*, 4:359–373 (1965).

Yeh et al., "Nicotine and Cotinine Inhibit Rat Testis Androgen Biosynthesis In Vitro", *J. Steriod Biochem.*, 33:627–630 (1989).

G. Kyerematen et al., "Disposition of nicotine and eight metabolites in smokers and nonsmokers: identification in smokers of two metabolites that are longer lived than nicotine," *Clin. Pharmacol. Ther.*, 48, 641–651 (1990).

W. Luck et al., "Extent of nicotine and cotinine transfer to the human fetus, placenta and amniotic fluid of smoking mothers," *Dev. Pharmacol. Ther.*, 8, 384–395 (1985).

C. Lynch et al., "Spontaneous cigarette brand switching: consequences for nicotine and carbon monoxide exposure," *Am. J. Public Health*, 78, 1191–1194 (1987).

R. C. O'Neill, "Tobacco products containing nicotine antagonists," *Chemical Abstracts*, 55, 16920 (1961).

E. Rylander et al., "Exposure to environmental tobacco smoke and urinary excretion of cotinine and nicotine in children," *Acta Poediatr. Scand.*, 78, 449–450 (1989).

I. Sasson et al., "Cigarette smoking and neoplasia of the uterine cervix: smoke constituents in cervical mucus," *New England J. Med.*, 312, 315–316 (1985).

K. Takada, et al., "Discriminitive stimulus effects of intravenous 1–nicotine and nicotine analogs or metabolites on squirrel monkeys," *Psychopharmacology*, 99, 208–212 (1989).

B. Testa et al., "Circular Dichroic determination of the preferred conformation of nicotine and related chiral alkaloids in aqueous solution," *Mol. Pharmacol.*, 9, 10–16 (1973).

R. Barbieri et al., "Cotinine and nicotine inhibit human fetal adrenal 11β–hydroxylase," *J. Clin. Endocrinol. Metab.*, 69, 1221–1224 (1989).

A. H. Beckett et al., "A possible relationship between pKa1 and lipid solubility and the amounts secreted in urine to some tobacco alkaloids given to man," *J. Pharma. Pharmacol.*, 24, 115–120 (1972).

M. Curvall et al., "Stimulation and evaluation of nicotine intake during passive smoking: cotinine measurements in body fluids of nonsmokers given intravenous infusions of nicotine," *Clin. Pharmacol. Ther.*, 47, 42–49 (1990).

J. Gabrielsson et al., "Constant–rate infusion of nicotine and cotinine. I. A physiological pharmacokinetic analysis of the cotinine disposition, and effects on clearance and distribution in the rat," *J. Pharmacokinetics Biopharmaceutics*, 15, 583–599 (1987).

R. Galeazzi et al., "Steady–stroke concentration of cotinine as a measure of nicotine–intake by smokers," *Eur. J. Clin. Pharmacol.*, 28, 301–304 (1985).

P. Jacob et al., "Disposition kinetics of nicotine and cotinine enantiomers in rabbits and beagle dogs," *J. Pharmaceutical Sciences*, 77, 396–400 (1988).

B. Kuo et al., "Influence of nicotine and continine on the expression of plasminogen activator activity in bovine aortic endothelial cells," *Thromb. Haemostasis*, 61, 70–79 (1989).

Chemical Abstracts, vol. 55, No. 17, 1961, Columbus, Ohio, U.S.; "Tobaccoo Products Containing Nicotine Antagonists", col. 16920.

N. L. Benowitz et al., Clin. Pharm. Ther., vol. 34, pp. 604–611 (1988) "Cotinine disposition and effects".

Benowitz, et al *Clin. Pharmacol. Ther* vol. 34, No. 5 (1983) pp. 604–611.

THERAPEUTIC METHOD TO ALLEVIATE THE CRAVING ASSOCIATED WITH CESSATION OF TOBACCO WITH COTININE

BACKGROUND OF THE INVENTION

Cigarette smoking continues to be the major preventable cause of death in the United States resulting in nearly 400,000 deaths per year due to cancer and heart disease. Despite the potential adverse health effects, the vast majority of cigarette smokers are unable to cease smoking.

The lack of smoking cessation success is thought to be related to the tobacco withdrawal syndrome or tobacco abstinence syndrome that most smokers experience during their attempts to quit. See, Office of Smoking and Health, *The Health Consequences of Smoking: Nicotine Addiction. A Report to the Surgeon General,* U.S. Govt. Print. Off., Washington D.C., DHHS Pub. No. (CDC) 88–8406 (1988). The most common effects are similar to those in almost all abstinence syndromes, and include decreased heart rate, anxiety, difficulty concentrating, impatience, irritability and restlessness. See, American Psychiatric Assoc., *Diagnostic and Statistical Manual,* Washington D.C. (3rd ed. 1980) at pages 159–160, 176–178. Most withdrawal effects occur within 24 hours, peak in the first 1–2 weeks and significantly decrease at one month. It is widely believed that the effects of abstinence from tobacco are due to nicotine deprivation, and that abstinence effects from smoking prevent smokers from stopping. See, J. R. Hughes et al., in *Research and Advances in Alcohol and Drug Problems, Vol.* 10, L. T. Kozlowski et al., eds., Plenum Pub. Corp. (1990) at pages 317–398.

Of the pharmacological approaches to aiding cessation of smoking, nicotine replacement, e.g., via transdermal nicotine patches or nicotine gum is the most widely used. Nicotine gum decreases abstinence discomfort, especially anxiety, decreased memory and irritability. On the other hand, nicotine gum does not reliably decrease weight gain or craving. Also, discontinuing use of nicotine gum leads to some of the same symptoms as the cigarette withdrawal syndrome. Furthermore, nicotine is toxic, and the availability of nicotine gum or patches poses a risk of poisoning to children and pets.

Other studies have demonstrated that alpha-2 agonists, such as clonidine, decrease postcessation anxiety, irritability and difficulty concentrating. Decreased sympathetic activity has been postulated to be the mechanism by which these drugs decrease abstinence effects. Although tobacco abstinence has some effects that could be attributed to sympathetic activity, it lacks the typical signs and symptoms of sympathetic overactivity, such as tachycardia, diaphoresis and hypertension. Thus, the mechanism by which alpha-2 agonists exert their effects is unclear. While a number of other pharmacological treatments, such as use of doxepin, ACTH, and corticotrophins, for abstinence symptoms have been tested, none of the studies reported baseline and postcessation values for abstinence symptoms. See, for example, S. J. Bourne (U.S. Pat. No. 4,621,074).

Therefore, a continuing need exists for pharmacological treatments that will facilitate smoking cessation, e.g., by blocking or relieving tobacco withdrawal syndrome, or reducing the symptoms of nicotine withdrawal.

SUMMARY OF THE INVENTION

The present invention provides a therapeutic method of treatment to (a) alleviate tobacco withdrawal syndrome (TWS), or (b) alleviate the similar abstinence effects due to cessation of nicotine alone comprising administering to a human in need of such treatment, i.e., a smoker or abstinent smoker, an amount of cotinine or a pharmaceutically acceptable salt thereof, in an amount effective to significantly reduce or eliminate at least one of the symptoms of TWS or of nicotine withdrawal. As discussed above, the symptoms of both tobacco and nicotine withdrawal are similar and are art recognized to include craving for tobacco, anxiety, irritability, insomnia, impatience, restlessness, difficulty concentrating, increased appetite/weight gain and decreased heart rate. The present method is effective both to alleviate TWC acutely and to permit patients to maintain abstinence for extended periods of time.

In a preferred embodiment, the present invention also provides a therapeutic method to alleviate the craving for cigarettes, tobacco and/or nicotine that is associated with cessation of tobacco use, e.g., by chewing or smoking, by the administration of an effective amount of cotinine or a pharmaceutically acceptable salt thereof, to a human in need of such treatment. However, the present invention is also useful to treat the symptoms of nicotine withdrawal which are due, for example, to cessation of use of nicotine gum or a nicotine transdermal patch.

The present invention is exemplified by a study in which (−)-cotinine base was intravenously administered to abstinent cigarette smokers. The cotinine administration caused many subjective changes without significantly altering cardiovascular activity. While cotinine administration appeared to mildly exacerbate some of the symptoms of the tobacco withdrawal syndrome such as anxiety, restlessness and the overall withdrawal syndrome checklist (WSC) subtotal score, it simultaneously decreased the number of withdrawal symptoms rated as greater than mild, and reduced the severity of some of the more severe withdrawal symptoms, including drowsiness. Cotinine also reduced the overall craving for cigarettes, tobacco and/or nicotine experienced during the session.

Cotinine has many qualities which can enhance its value as a smoking cessation aid. Cotinine has a long in vivo half-life, complete oral bioavailability, minimal effect on the cardiovascular system, and not been reported to be harmful even at very high doses in many species including man. Also, because cotinine has no significant effect on the heart, a combined pharmacologic treatment approach using cotinine and nicotine may be possible.

The present invention also provides an article of manufacture comprising packaging material, such as a box, bottle, tube, sprayer, insufflator, intravenous (i.v.) bag, envelope and the like; and at least one unit dosage form of a pharmaceutical agent contained within said packaging material, wherein said pharmaceutical agent comprises cotinine or a pharmaceutically acceptable salt thereof in an amount effective to alleviate tobacco withdrawal syndrome, the symptoms of nicotine withdrawal or the craving associated with cessation of tobacco smoking, and wherein said packaging material includes instruction means which indicate that said cotinine or said pharmaceutically acceptable salt thereof can be used for alleviating tobacco withdrawal syndrome, the symptoms of nicotine withdrawal or the craving associated with the cessation of tobacco smoking. Suitable instruction means include printed labels, printed package inserts, tags, cassette tapes, and the like.

DETAILED DESCRIPTION OF THE INVENTION

Cotinine

Cotinine (1-methyl-5-(3-pyridinyl)-2-pyrrolidinone) has the formula shown below:

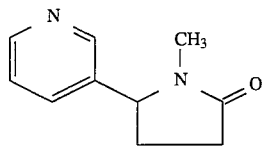

The physiologically active form is the (−)-isomer, so as used herein, the term "cotinine" includes (−)-cotinine, or the racemic form, (±)-cotinine. The free base, depicted above, can be employed in the practice of the invention, as can the pharmaceutically acceptable salts. These include the amine-acid addition salts of nontoxic organic acids or inorganic acids, such as the tartarate, fumarate ("scotine"), citrate, maleate, malate, hydrobromide, hydrochloride, sulfate, phosphate and the like. For example, see F. Vaitekunas, *J. Amer. Chem. Soc.*, 79, 149 (1957). E. R. Bowman et al., in *J. Pharmacol. and Exp. Ther.*, 135, 306 (1962) report the preparation of (−)-cotinine free base from (−)-nicotine. The preparation and purification of (−)-cotinine fumarate is described by N. L. Benowitz et al., *Clin. Pharmacol. Ther.*, 34, 604 (1983).

Cotinine is the major metabolite of nicotine which accumulates in the body as a result of nicotine exposure and has previously been believed to be pharmacologically inactive. For example, see N. L. Benowitz, "The use of biologic fluid samples in assessing tobacco smoke consumption", in *Measurement in the Analysis and Treatment of Smoking Behavior*, J. Grabowski et al. eds., *NIDA Research Monograph No. 48, U.S. DHHS, PHS, ADAMHA* (1983). In contrast to nicotine, cotinine has a relatively long terminal elimination half-life (two versus sixteen hours, respectively). Due to this pharmacological characteristic, cotinine has become the principally used objective biochemical marker of nicotine exposure in cigarette smoking and/or cessation-related research paradigms.

While cotinine is a well-known metabolite of nicotine and is routinely measured in many laboratories, no systematic investigation of the physiological and subjective effects produced by intravenous cotinine administration has been performed in humans. K. I. Yamamoto et al., *International J. Neuropharmacol.*, 4, 359 (1965) reported that intravenous cotinine produced increases in EEG activity and behavioral arousal in cats with only a slight decrease in blood pressure. In squirrel monkeys, intramuscular cotinine injections increased rates of responding on fixed interval schedules of reinforcement over a wide range of doses (M. E. Risner et al., *J. Pharmacol. and Exp. Ther.*, 234, 113 (1985); S. R. Goldberg et al., *Psychopharmacology*, 97, 295 (1989)). These findings, taken together, suggest that cotinine acts as a psychomotor stimulant. However, the pharmacologic mechanism of action has yet to be determined.

In two recent human studies, the pharmacokinetic profiles of intravenous and orally administered cotinine were examined without emphasis on measuring the subjective and/or physiological changes induced by this compound (N. L. Benowitz et al., *Clin. Pharmacol. and Therapeutics*, 34, 604 (1983); P. J. DeSchepper et al., *Eur. J. Pharmacol.*, 31, 583 (1987)). Moreover, using an uncontrolled experimental design, Benowitz et al., *Clin. Pharm. and Ther.*, 34, 604 (1988), found that intravenous cotinine produced no cardiovascular changes and only slight differences in various subjective ratings which were comparable to placebo-induced changes found in other experiments with nicotine. Consequently, Benowitz and his colleagues concluded that cotinine lacked significant pharmacologic activity in humans.

Administration and Dosages

While it is possible that, for use in therapy, cotinine and/or its salts may be administered as the pure chemicals, as by inhalation of a fine powder via an insufflator, it is preferable to present the active ingredient as a pharmaceutical formulation. The invention thus further provides a pharmaceutical formulation comprising cotinine and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the cotinine from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the cotinine may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279, 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhaler or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the cotinine can be administered as drops, gels (see, S. Chrai et al., U.S. Pat. No. 4,255,415), gums (see S.-L. Lin et al., U.S. Pat. No. 4,136,177) or via a prolonged-release ocular insert (see A. S. Michaels, U.S. Pat. No. 3,867,519 and H. M. Haddad et al., U.S. Pat. No. 3,870,791).

The pharmaceutical compositions according to the invention may also contain other adjuvants such as flavorings, colorings, antimicrobial agents, or preservatives.

It will be further appreciated that the amount of cotinine, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day, calculated as (−)-cotinine in the free base form.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will be further described by reference to the following detailed Example.

Example I - Intravenous Administration of (−)-Cotinine

A. Subjects: Participants included 18 healthy male volunteers between the ages of 18 and 40 years old who had 1) no history of psychiatric, alcohol and drug abuse disorders, 2) smoked at least one pack of cigarettes per day for one year prior to study admission, 3) an expired-air carbon monoxide concentration of greater than 20 ppm, 4) not currently on any medication, and 5) not donated blood in the past 90 days. Potential subjects were carefully screened for physical and mental health problems.

B. Drug Preparation and Administration Procedures: (−)-Cotinine base was synthesized from (−)-nicotine using the bromine-zinc oxidation method described by E. R. Bowman et al., *Biochem. Preparations,* 10, 36 (1963). Hereinafter, the term "cotinine" will be used to refer to (−)-cotinine. The cotinine base was analyzed for impurities using gas chromatography/mass spectrometry and thin layer chromatography and found to be pure. Using sterile techniques, cotinine solution was prepared for intravenous administration. Cotinine base was combined with sterile normal saline solution to achieve a concentration of three mg of cotinine base per one ml of solution. This solution was autoclaved and found to be non-pyrogenic using a standard pyrogenicity testing. The cotinine solution was again tested for molecular structure integrity and concentration accuracy. Next, 10 ml of cotinine solution (30 mg cotinine) were placed into 20 ml injection vials, sealed and stored in a refrigerator until used. The placebo was ten ml of sterile normal saline solution. Placebo and active drug vials were prepared and labeled in a double-blind manner by pharmacy personnel. In addition to pharmacy personnel, one study physician who had no contact with subjects during the experimental sessions had access to the drug code in the event of a medical emergency.

During sessions, subjects received 10 ml (30 mg) of cotinine base solution diluted to 15 ml with sterile normal saline solution or placebo (15 ml of sterile saline solution) infused intravenously through a 20 gauge indwelling intravenous catheter. This infusion rate was chosen so as not to exceed two mg per minute of cotinine delivered to the subject. Infusions were performed using a controlled-rate syringe infusion pump. All subjects received cotinine and placebo infusions using a randomly assigned double-blind counterbalanced-order design.

C. Dependent Measures: The physiological parameters monitored included heart rate, systolic, diastolic and mean arterial blood pressure, and a 12-lead electrocardiogram (ECG) with measurement of PR, QRS and QT intervals. The biochemical parameters included expired-air carbon monoxide level (CO), serum nicotine and cotinine concentrations. Carbon monoxide was measured using standard techniques. The serum nicotine and cotinine concentration assays were performed using gas chromatography and mass spectrometry at the Laboratory of Physiological Hygiene at the University of Minnesota Medical School.

Self-reported ratings of subjective state, mood and cigarette withdrawal symptoms were obtained from the subjects. These measures included the Profile of Mood States questionnaire (POMS), several 100 mm visual analog scales (VAS) and the cigarette withdrawal symptoms checklist (WSC) of symptoms related to the cigarette withdrawal syndrome (J. R. Hughes et al., *Archives of General Psychology*, 43, 289, (1986)). The Record of Withdrawal Symptom is a 0=(none) - 5=(severe) scale of 12 symptoms associated with TWS: craving, irritable/angry, anxious/tense, difficulty concentrating, restless, impatient, excessive hunger, insomnia, increased eating, drowsiness, headaches and miscellaneous group including tremor, heart racing, sweating, dizzy or g.i. problems.

Two VAS forms were used. One with 11 adjectives including "Pleasant", "Need for Cigarettes", "Energy", "Hungry", "Down", "Sedated", "Anxious", "Stimulated", "Fatigue", "Craving for Cigarettes" and a separate VAS for "Craving for Tobacco". Also, an adverse effects questionnaire (AEQ) was used to assess possible problems associated with cotinine administration. These problems were restlessness, headaches, tachycardia/palpatations, tremor, excessive sweating, nausea/vomiting, upset stomach, lightheadedness/dizzy, drowsy, irritable, and excessive salivation. The symptoms assessed were those known to be experienced following nicotine administration.

D. Procedure: This study was performed on an outpatient basis over nine days. Subjects were required to attend five sessions. All sessions were held at the Tobacco Research Laboratory associated with the University of Minnesota Hospital Complex, Minneapolis, Minn. The first session was used to obtain informed consent, physical and psychological screening of the prospective participant, background and baseline data collection. Also, the subject habituated to the data collection procedures to be utilized during the sessions. If the participant met inclusion criteria, the participant was scheduled for his next visit. Prior to session 2, the subject was randomly assigned to one of the two drug administration order conditions.

Sessions 2 and 4 were used for baseline measurement of all variables under conditions of ad libitum cigarette smoking. These sessions occurred between 5 and 7 pm, and lasted about 15 minutes. Vital signs, CO, WSC, VAS, POMS and AEQ were completed. Also, blood was drawn for later measurement of serum nicotine and cotinine concentration. Sessions 2 and 4 were held seven days apart and began at the same time as sessions 3 and 5. After departing the laboratory, the subjects were required to refrain from cigarette smoking and other forms of tobacco use over the next 48 hours, at which time they were to report back to the laboratory for their drug infusion session.

During sessions 3 and 5, subjects received cotinine or placebo infusions in a counterbalanced order. Sessions 3 and 5 were held 48 hours after sessions 2 and 4 during which time the subject was tobacco abstinent. After the subject reported to the laboratory, baseline measurements of CO, vital signs, WSC, VAS, POMS and AEQ were made. Next, the ECG electrodes were attached to the chest wall and limbs. For intravenous drug administration and access in the event of an adverse event, a 20 gauge indwelling catheter was placed in a prominent vein in the non-dominant forearm. This allowed the subject to freely complete subjective effects questionnaires during the remainder of the session. Heart rate and blood pressure were recorded. Using standard venipuncture techniques, five mls of blood were drawn from the antecubital area of the dominant arm for later serum nicotine and cotinine concentration analyses. At intervals of 5, 15, 30, 60 and 120 minutes after the drug infusion, heart rate, blood pressure, ECG, WSC, VAS, and AEQ were completed, and blood was drawn for later serum nicotine and cotinine concentration analyses. Also, the POMS was completed at 30, 60 and 120 minutes after drug administration.

E. Statistical Analyses: All questionnaires were scored and entered into a computer by a blinded research assistant. At the end of the experiment and when all data scoring, collation and entry were completed, the drug code and serum cotinine concentrations were entered into the computer.

Due to a small sample size and large response variability, statistical analyses included the use of a priori predictions of the direction of effects and one-tailed paired T-test comparisons of difference scores. Three sets of analyses were undertaken. First, a comparison of the baseline measurements recorded during ad libitum cigarette smoking and after 48 hours of cigarette abstinence prior to receiving the drug infusion. Second, cotinine versus placebo session comparisons of the area under the curve (AUC) calculated using the trapezoid rule and divided by the total time (2 hours). Also, difference scores produced by subtracting the AUC from the baseline score were utilized. For the POMS analyses, pre- and post-session difference scores were used. Also, an additional set of cotinine versus placebo session comparisons were performed on the difference scores generated by subtracting the maximum decrease from baseline on the various measurements of craving for cigarettes, tobacco and nicotine. Statistical significance was defined as a p-value equal to or less than 0.05 probability of a chance occurrence.

F. Results: Eighteen male cigarette smokers who were required to be abstinent prior to receiving the drug infusions in sessions 3 and 5 participated. Upon receipt of the serum cotinine concentration data, four subjects were found not to be abstinent from cigarette smoking during the abstinence phases. Their data was excluded from subsequent statistical analyses. Of the four data sets removed, two received drug first and two received placebo first maintaining the counterbalanced-order design. The data presented herein represent those collected from the 14 study-compliant completing participants.

The participants were healthy male cigarette smokers whose average age was 25.6 years (SD=6.5). None of the participants were interested in cigarette smoking cessation. They smoked an average of 25.4 (SD=6.0) cigarettes per day. Their average expired-air carbon monoxide concentration was 9.1 (SD=7.3). Their average expressed-air carbon monoxide concentration was 28.1 ppm (SD=10.3). The average FTC estimated nicotine yield of their cigarettes was 0.87 (SD=0.3). Their average baseline serum cotinine concentration was 378 (SD=16.3). Their mean education level was 14.5 years (SD=1.7).

The biochemical variables of interest included the serum cotinine and nicotine concentrations. The average baseline serum cotinine concentrations for the sessions were as follows (ng/ml): Session 2: 378 (SE=43) Session 3: 48 (SE=5.8); Session 4: 308 (SE=24); and Session 5: 54 (SE=6.7). The average baseline serum nicotine concentrations (ng/ml) for sessions 3 and 5 were 0.4 (SE=0.2) and 0.2 (SE=0.2), respectively. Also in Table 1, the sessional changes in serum cotinine and nicotine concentrations are listed. These values represent the session end minus session beginning concentrations. Serum cotinine concentration increased by 430 ng/ml of serum in the cotinine condition and decreased 11 ng/ml in the placebo condition (T(13)=

TABLE 1

PHYSIOLOGIC MEASURES

| Variable | Cotinine Mean (SE) | Placebo Mean (SE) | Difference Mean (SE) | T-value | P-value (one-tailed) |
|---|---|---|---|---|---|
| Heart Rate (BPM) | 63.9 (1.6) | 64.4 (1.9) | −0.5 (1.8) | −0.27 | ns |
| Systolic Blood Pressure (mmHg) | 118 (5.1) | 118 (4.8) | 0.4 (1.9) | 0.2 | ns |
| Diastolic Blood Pressure (mmHg) | 71.7 (2.6) | 74.2 (2.9) | −2.5 (1.4) | −1.76 | 0.05 |
| Mean Arterial Pressure (mmHg) | 86.8 (3.1) | 88.7 (3.3) | −1.9 (0.9) | −1.53 | 0.07 |
| Serum Cotinine Concentration* (session change) | 430 (26) | −11 (2.3) | 441 (27) | 16.4 | 0.001 |
| Serum Nicotine Concentration* (session change) | 0.1 (0.1) | 0.0 (0.1) | 0.1 (0.2) | 0.6 | ns | ns = non-significant
* = ng/ml

In Table 1, the physiologic and biochemical measures of interest are listed. The cardiovascular measures represent the area under the curve calculated using the trapezoid rule divided by the total session time (two hours). This produced a time-weighted measurement for the particular parameter under study. As was apparent, intravenous cotinine administration had no effect on heart rate or the electrocardiographic intervals (e.g., PR, QRS and QT). Cotinine produced a slight decrease in diastolic blood pressure (p=0.05).

16.4; p =0.001). More importantly, the serum nicotine concentration showed no change during the session which rules out the possibility of unanticipated nicotine administration as the agent responsible for the reported subjective and cardiovascular effects in this experiment. The observed change in nicotine concentration was consistent with the limits of sensitivity of the analyses (SEM=±1 ng/ml).

TABLE 2

SUBJECTIVE MEASURES

| Variable | Cotinine Mean (SE) | Placebo Mean (SE) | Difference Mean (SE) | T-value | P-value (one-tailed) |
|---|---|---|---|---|---|
| PLEASANT (VAS-1) | 45.5 (3.7) | 53.1 (3.6) | −7.6 (3.3) | −2.27 | 0.02 |
| SEDATED (VAS-1) | 28.9 (4.3) | 36.3 (5.8) | −7.4 (2.8) | −2.72 | 0.01 |
| IRRITABLE (WSC) | 1.5 (0.3) | 0.9 (0.2) | 0.6 (0.9) | 2.21 | 0.03 |
| ANXIOUS (WSC) | 1.9 (0.3) | 1.2 (0.2) | 0.7 (0.2) | 3.11 | 0.005 |
| RESTLESSNESS (WSC) | 1.6 (0.3) | 1.1 (0.3) | 0.5 (0.3) | 1.57 | 0.07 |
| WSC SUBTOTAL SCORE | 9.5 (1.4) | 6.9 (1.0) | 2.6 (1.4) | 1.84 | 0.05 |
| NUMBER OF WSC SUBTOTAL SYMPTOMS CHANGE | −2.7 (0.5) | −1.8 (0.4) | −0.9 (0.5) | −1.86 | 0.05 |
| STIMULATED CHANGE (VAS-1) | −8.9 (3.9) | −22.9 (5.6) | 14.0 (6.0) | 2.34 | 0.02 |
| DROWSINESS | −0.9 (0.3) | −0.2 (0.3) | −0.7 (0.4) | −1.77 | 0.05 |

TABLE 2-continued

| | SUBJECTIVE MEASURES | | | | |
|---|---|---|---|---|---|
| Variable | Cotinine Mean (SE) | Placebo Mean (SE) | Difference Mean (SE) | T-value | P-value (one-tailed) |
| CHANGE (WSC) DROWSY | −0.3 (0.3) | −0.0 (0.3) | −0.3 (0.15) | −2.04 | 0.03 |
| CHANGE (AEQ) HEADACHES | 0.0 (0.1) | −0.2 (0.1) | −0.2 (0.1) | −1.85 | 0.05 |
| CHANGE (AEQ) POMS-CONFUSION CHANGE SCORE | −0.7 (0.7) | −2.7 (1.1) | 2.0 (1.1) | 1.76 | 0.05 |

In Table 2, the subjective ratings of mood and cigarette withdrawal symptoms are listed. Throughout the cotinine session, the subjects rated themselves as feeling less pleasant (p=0.02), less sedated (P=0.01), more irritable (p=0.03), more anxious (p=0.005) and more restless (p=0.03). However, the subjects reported a greater decrease in drowsiness (p=0.03; p=0.05), and a smaller decrease in stimulation (p=0.02), headaches (p=0.05) and the POMS subscale for confusion (p=0.05) during the cotinine sessions. Also, while the subjects reported an overall increased severity of their cigarette withdrawal symptoms (p=0.05) during the cotinine session, a simultaneous decrease in the number of the more severe cigarette withdrawal symptoms (those rated greater than "mild") (p=0.05) was observed during the same session. The increase in the overall withdrawal score most likely reflects a mild increase in symptoms (such as anxiety, restlessness, irritability) which are measured as indicators of cigarette withdrawal severity, but could be increased mildly as a result of psychomotor stimulant properties of cotinine. Therefore, the observed withdrawal severity increase probably reflects an increase in symptoms which are not specific to the tobacco withdrawal syndrome. This was supported by the overall decrease in the total number of more severe withdrawal symptoms reported as a function of cotinine administration.

Statistical analyses on the various measures of craving using data from both experimental sessions yielded no significant differences. This was due to immense variability generated by the subjects in the third session. Due to the use of the intravenous route of administration, subjects showed substantial drug and placebo effects which appeared to be attenuated in session five. Therefore, in an attempt to eliminate this great variability, a reanalysis of the data comparing cotinine versus placebo on the maximum sessional decrease from baseline in the various craving measures was performed using only session five data. The results are summarized in Table 3. The "Craving for Tobacco" visual analog score (p=0.02) and the average of all craving scales (p=0.05) were significantly decreased in the cotinine condition compared to placebo. The average of all craving scores was achieved using the WSC "craving for nicotine" score multiplied by 20 and then adding all of the scores and dividing this number by four. There was a consistent directional effect across all measures with the cotinine showing a greater influence than placebo.

TABLE 3

| | MAXIMUM CRAVING DECREASE SCORE | | | | |
|---|---|---|---|---|---|
| Variable | Cotinine Mean (SE) | Placebo Mean (SE) | Difference Mean (SE) | T-value | P-value (one-tailed) |
| Need for Cigarettes (VAS-1) | −24.8 (6.3) | −13.7 (2.7) | −11.1 (6.8) | −1.63 | 0.07 |
| Craving for Cigarettes (VAS-1) | −19.6 (4.7) | −16.3 (2.7) | −3.3 (5.5) | −0.59 | ns |
| Craving for Tobacco (VAS-2) | −25.6 (3.8) | −14.3 (3.1) | −11.3 (4.8) | −2.33 | 0.02 |
| Craving for Nicotine (WSC) | −1.56 (.18) | −1.11 (.26) | −0.45 (.32) | −1.41 | 0.09 |
| Average of All Craving Scales (VAS-1, -2, WSC) | −24.9 (2.8) | −17.4 (3.2) | −7.5 (4.2) | −1.77 | 0.05 | ns = non-significant

G. Discussion: The purpose of the study was to determine whether intravenously administered (−)-cotinine base has significant pharmacologic activity in abstinent cigarette smokers. The data presented herein is the first demonstration that cotinine is a pharmacologically active compound which produces many subjective changes in humans without significantly affecting cardiovascular activity. Further, while cotinine administration appeared to exacerbate certain symptoms of the tobacco withdrawal syndrome, it simultaneously attenuated the total number of reported withdrawal symptoms and the craving (for tobacco, nicotine and cigarettes) experienced during the session. Cotinine exacerbated irritability, anxiety, restlessness and the overall WSC subtotal score, while decreasing the frequency of the more severe symptoms reported such as confusion.

Increases in withdrawal scores are usually attributable to an increased severity of the cigarette abstinence syndrome; however, other explanations exist. First, higher serum cotinine concentrations (in the absence of nicotine) could serve to exacerbate symptoms of the cigarette withdrawal syndrome and may be partially responsible for relapse to cigarette smoking, especially in the heaviest smokers because of their high cotinine level. Another explanation stems from cotinine's psychomotor stimulant activity. Acutely, psychomotor stimulant use typically makes people feel more anxious, irritable, restless and impatient until they become tolerant to these effects. Therefore, its stimulant activity may be increasing symptoms which are not specific to the cigarette withdrawal syndrome. One last explanation should also be considered. Cotinine may have produced the "priming effect." That is, cotinine administration may have produced a subjective state similar to that associated with nicotine abstinence, and subsequent nicotine use. As a result, these abstinent cigarette smokers may have responded in a manner similar to that experienced during tobacco withdrawal. While the priming effect is seen with low dose administration, higher doses of drug usually satiate the organism's appetite for further drug self-administration.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A therapeutic method to alleviate the craving associated with cessation of tobacco smoking comprising administering an amount of cotinine or a pharmaceutically acceptable salt thereof, to a human in need of such treatment, which amount is effective to alleviate craving for at least one of cigarettes, tobacco or nicotine.

2. The method of claim 1 wherein the cotinine is (−)-cotinine.

3. The method of claim 2 wherein the cotinine is a salt of (−)-cotinine.

4. The method of claim 1 wherein the cotinine or the pharmaceutically acceptable salt thereof is administered orally.

5. The method of claim 4 wherein the cotinine or the pharmaceutically acceptable salt thereof is orally administered by means of a chewing gum.

6. The method of claim 1 wherein the cotinine or the pharmaceutically acceptable salt thereof is administered parenterally.

7. The method of claim 6 wherein the cotinine or the pharmaceutically acceptable salt thereof is administered by means of a transdermal patch.

8. The method of claim 6 wherein the cotinine or the pharmaceutically acceptable salt thereof is administered intraocularly.

9. The method of claim 8 wherein the cotinine or the pharmaceutically acceptable salt thereof is administered via an intraocular insert.

10. The method of claim 6 wherein the cotinine or the pharmaceutically acceptable salt thereof is administered intravenously.

11. The method of claim 6 wherein the cotinine or the pharmaceutically acceptable salt thereof is administered intranasally.

12. The method of claim 1 wherein the amount is sufficient to deliver a dose of cotinine from about 0.4 mg/kg to about 15 mg/kg.

13. The method of claim 1 wherein the amount is sufficient to deliver a dose of cotinine from about 1 mg/kg to about 100 mg/kg.

14. A therapeutic method to aid in cessation of, or maintain abstinence from, tobacco use comprising administering an amount of cotinine or a pharmaceutically acceptable salt thereof, to a human in need of such treatment, which amount is effective to aid in cessation of, or maintain abstinence from, tobacco use.

15. The method of claim 14 wherein the cotinine is (−)-cotinine.

16. The method of claim 15 wherein the cotinine is a salt of (−)-cotinine.

17. The method of claim 14 wherein the cotinine or the pharmaceutically acceptable salt thereof is administered orally.

18. The method of claim 17 wherein the cotinine or the pharmaceutically acceptable salt thereof is orally administered by means of a chewing gum.

19. The method of claim 14 wherein the cotinine or the pharmaceutically acceptable salt thereof is administered parenterally.

20. The method of claim 19 wherein the cotinine or the pharmaceutically acceptable salt thereof is administered by means of a transdermal patch.

21. The method of claim 19 wherein the cotinine or the pharmaceutically acceptable salt thereof is administered intraocularly.

22. The method of claim 21 wherein the cotinine or the pharmaceutically acceptable salt thereof is administered via an intraocular insert.

23. The method of claim 19 wherein the cotinine or the pharmaceutically acceptable salt thereof is administered intravenously.

24. The method of claim 19 wherein the cotinine or the pharmaceutically acceptable salt thereof is administered intranasally.

25. The method of claim 14 wherein the amount is sufficient to deliver a dose of cotinine from about 0.4 mg/kg to about 15 mg/kg.

26. The method of claim 14 wherein the amount is sufficient to deliver a dose of cotinine from about 1 mg/kg to about 100 mg/kg.

* * * * *